(12) United States Patent
Bazin et al.

(10) Patent No.: US 7,986,987 B2
(45) Date of Patent: Jul. 26, 2011

(54) DEVICE, SYSTEM AND METHOD FOR OBSERVING A TYPOLOGICAL CHARACTERISTIC OF THE BODY

(75) Inventors: Roland Bazin, Bievres (FR); Franck Giron, Ferrieres-En-Brie (FR)

(73) Assignee: L' Oréal, Paris (FR)

( * ) Notice: Subject to any disclaimer, the term of this patent is extended or adjusted under 35 U.S.C. 154(b) by 466 days.

(21) Appl. No.: 10/183,625

(22) Filed: Jun. 28, 2002

(65) Prior Publication Data

US 2003/0045799 A1  Mar. 6, 2003

(30) Foreign Application Priority Data

Jul. 9, 2001  (FR) .................................... 01 09091

(51) Int. Cl.
*A61B 6/00* (2006.01)
(52) U.S. Cl. ........ 600/407; 600/424; 600/428; 600/473; 600/475; 600/476; 600/478; 600/479
(58) Field of Classification Search .......... 600/476–477, 600/407, 424, 428, 473, 475, 478, 479; 606/2–19
See application file for complete search history.

(56) References Cited

U.S. PATENT DOCUMENTS

| | | | |
|---|---|---|---|
| 1,339,698 A * | 5/1920 | Faix et al. .......................... 7/118 |
| 4,911,544 A | 3/1990 | Walsh | |
| 5,138,421 A | 8/1992 | Saito | |
| 5,146,923 A * | 9/1992 | Dhawan ........................ 600/476 |
| 5,198,875 A * | 3/1993 | Bazin et al. .................... 356/369 |
| 5,311,293 A | 5/1994 | MacFarlane et al. | |
| 5,377,000 A * | 12/1994 | Berends .......................... 356/73 |
| 5,813,987 A * | 9/1998 | Modell et al. .................. 600/473 |
| 5,825,502 A * | 10/1998 | Mayer .......................... 358/296 |
| 5,954,658 A * | 9/1999 | Gorti .............................. 600/504 |
| 5,986,746 A * | 11/1999 | Metz et al. ...................... 356/71 |
| 6,032,071 A * | 2/2000 | Binder .......................... 600/476 |
| 6,070,092 A | 5/2000 | Kazama et al. | |
| 6,106,457 A * | 8/2000 | Perkins et al. ................. 600/175 |
| 6,111,653 A | 8/2000 | Bucknell et al. | |
| 6,178,340 B1 * | 1/2001 | Svetliza ........................ 600/310 |
| 6,353,753 B1 * | 3/2002 | Flock et al. .................... 600/473 |
| 6,485,413 B1 * | 11/2002 | Boppart et al. ................. 600/160 |
| 6,603,552 B1 * | 8/2003 | Cline et al. .................... 356/417 |
| 6,853,482 B1 * | 2/2005 | Kitamura et al. ............. 359/390 |
| 6,993,167 B1 * | 1/2006 | Skladnev et al. ............. 382/128 |
| 2003/0018271 A1 * | 1/2003 | Kimble .......................... 600/473 |

FOREIGN PATENT DOCUMENTS

| | | |
|---|---|---|
| EP | 0 655 211 | 5/1995 |
| EP | 0 913 681 A2 | 5/1999 |
| FR | 2 650 890 | 2/1991 |
| JP | 01-117756 | 8/1989 |
| JP | 3-65205 | 3/1991 |
| JP | 5-15500 | 1/1993 |
| JP | 6-095996 | 4/1994 |

(Continued)

*Primary Examiner* — Tse Chen
*Assistant Examiner* — Baisakhi Roy
(74) *Attorney, Agent, or Firm* — Oblon, Spivak, McClelland, Maier & Neustadt, L.L.P.

(57) ABSTRACT

A portable device for observing a typological characteristic of the body. For example, the device can be used to observe at least one characteristic of the appearance of the skin or the hair. The device can generate at least two images of the zone under examination. The images differ from each other as to a feature other than magnification and the intensity of the light source.

62 Claims, 9 Drawing Sheets

FOREIGN PATENT DOCUMENTS

| | | |
|---|---|---|
| JP | 6-95996 | 11/1994 |
| JP | 7-019839 | 1/1995 |
| JP | 07-71945 | 3/1995 |
| JP | 7-22655 | 5/1995 |
| JP | 07-143967 | 6/1995 |
| JP | 7-255704 | 10/1995 |
| JP | 7-289524 | 11/1995 |
| JP | 7-323013 | 12/1995 |
| JP | 2565679 | 12/1997 |
| JP | 10-127585 | 5/1998 |
| JP | 10-333057 | 12/1998 |
| JP | 11-064160 | 3/1999 |
| JP | 11-183371 | 9/1999 |
| JP | 3065205 | 10/1999 |
| JP | 3007978 | 12/1999 |
| JP | 2000-186998 | 7/2000 |
| JP | 2001-70251 | 3/2001 |
| JP | 2001-166219 | 6/2001 |
| WO | WO 96/16698 | 6/1996 |
| WO | WO 97/47238 | 12/1997 |
| WO | WO 98/24360 | 6/1998 |
| WO | WO 01/45557 | 6/2001 |

* cited by examiner

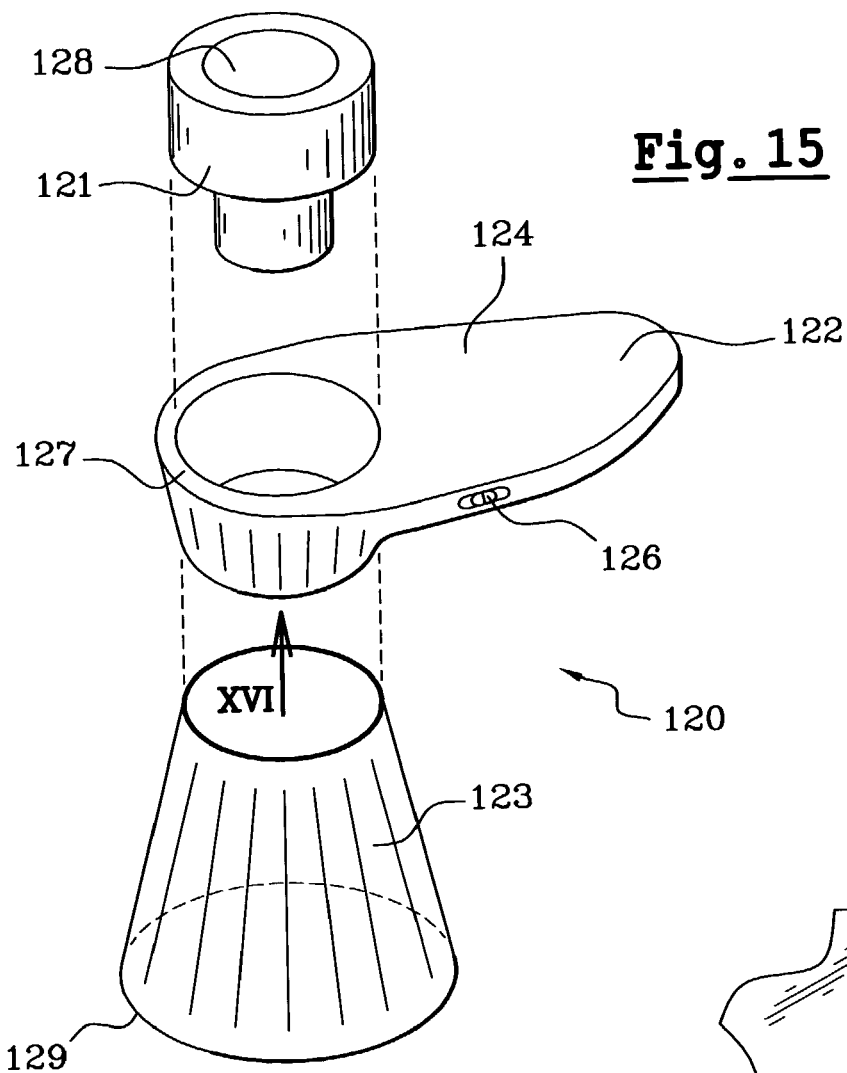
Fig. 15
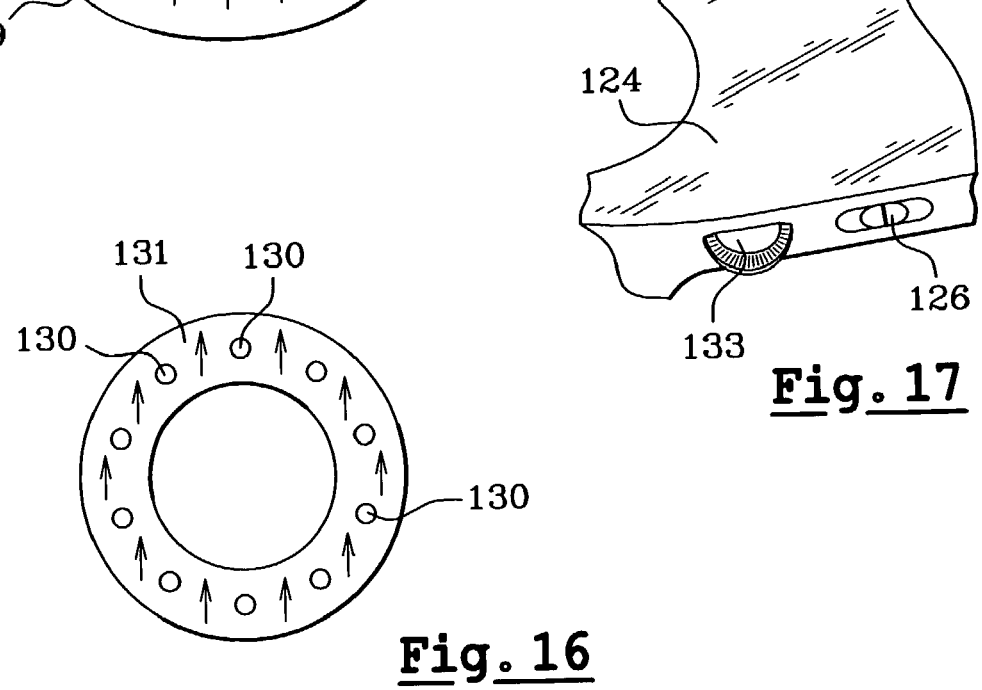
Fig. 16
Fig. 17

DEVICE, SYSTEM AND METHOD FOR OBSERVING A TYPOLOGICAL CHARACTERISTIC OF THE BODY

CROSS-REFERENCE TO RELATED APPLICATIONS

This document claims priority to French Application No. 0109091 filed Jul. 9, 2001, the entire content of which is hereby incorporated by reference.

BACKGROUND OF THE INVENTION

1. Field of the Invention

The present invention relates to evaluating typological characteristics of the body, in particular, characteristics of appearance such as, for example, brilliance, color, and cutaneous relief.

2. Description of the Background

Dermatoscopes with a magnifying system and integrated lighting sources are known. Such dermatoscopes, however, are not designed to deliver an image other than a mere magnification of the zone under observation. In addition, the lighting characteristics can vary from one dermatoscope to another. This variation is not of great significance when the purpose is to observe a defect of the skin, but is unsatisfactory when the purpose is to evaluate the characteristics of appearance, such as, for example, brilliance or color.

Complex systems using video cameras or other electronic sensors are also known, as described, for example, in European patent application EP-A-0 655 211 and U.S. Pat. No. 5,377,000. Those systems are relatively expensive and are ill-suited for widespread distribution, e.g., for use at all points of sale of a product or to enable members of the public to perform evaluations on themselves.

SUMMARY OF THE INVENTION

Consequently, there exists a need for an instrument that is simple to use, relatively inexpensive, and that enables the evaluation of at least one appearance characteristic of the skin or the hair, for example, characteristics associated with the radiant nature of skin complexion or hair, such as brilliance and color. One object of the present invention is to provide such an instrument. The present invention provides a novel portable observation device enabling at least one characteristic of body typology, such as the appearance of the skin and/or hair, to be evaluated.

In a preferred embodiment of the present invention, the device allows a user to observe a zone of the skin or the hair directly. The device generates at least two images of a zone under examination. These images differ from each other as to a feature other than their magnification or the intensity of the light source used to generate them, i.e., the difference under consideration is with respect to a difference other than magnification or intensity. Examples for such a differentiating feature include, but are not limited to, the orientation of the polarization direction of a polarizer, the degree of directivity of the incident light, the direction of incidence of the incident light, the color of the light, the filtering of the light coming from the zone under examination, or a mechanical action being exerted on the zone under examination (e.g., pressing, creasing, or stretching).

The images can be generated so as to be comparable with each other, either simultaneously or successively. The images can be generated successively by acting between two observations on a member of the device that varies a feature other than magnification or source light intensity. The device can include optical elements that produce two different images simultaneously of the zone under observation. The images can optionally be generated in such a manner as to tract variation in a zone under examination over time.

The observation device makes it possible to follow the way the zone of the skin varies over time. In a preferred embodiment, this can be accomplished by generating at a given instant at least two images of the zone of the skin, which images differ from each other as discussed above, and then generating (e.g., one month later) at least two images of the same zone of the skin, also differing from each other as discussed above.

The device of the invention allows direct observation (i.e., observation of the zone under examination by looking through the observation device without the need for acquiring an image by photographic, video, or other electronic types of acquisition). The production cost of the device can thus remain compatible with widespread distribution. Furthermore, since observation can be performed under predefined lighting conditions, it is possible to quantify the characteristic under observation in a manner that is relatively accurate and reproducible.

In a preferred embodiment, the device includes an optical system configured to produce a magnified image of the zone under examination. This optical system permits the user to observe skin characteristics that are difficult to observe with the naked eye, for example desquamation.

In another embodiment, the device is configured to reduce or eliminate the brilliance of at least a portion of the zone under examination. This feature can make it easier, for example, to observe the color of the skin or the hair, without being troubled by glinting reflections. Suppressing or reducing brilliance can also be useful in observing the color of backscattered light coming from deep layers of the skin or the hair, which color can depend on the state of these layers. In particular, it can be advantageous to observe the contrast between light which includes both a reflection component and a backscattered component, and light which essentially includes a backscattered component. This contrast can be achieved, for example, by illuminating the zone under examination under polarized light and by observing it with a polarization analyzer. The analyzer can include a rotary polarizer or a pair of polarizers having different polarization directions, one of which can be perpendicular to the polarization direction of the incident light and the other parallel to the polarization direction of the incident light.

In a particular embodiment, a lighting source illuminates the zone under examination with incident light under different angles of inclination. For example, the lighting source can illuminate the zone under examination with diffuse lighting and grazing light. A variety of conditions of observation are thus available. This variety facilitates the evaluation of some particular characteristic of appearance. For example, the differences between two images can be emphasized. Grazing light can provide information concerning relief, while diffuse lighting can provide information concerning uniformity of color.

In a particular embodiment, the device includes at least one screen located between the source of light and the zone under examination so as to illuminate the zone only with light diffusing beneath the screen in the tissue under examination. The screen can be movable between a first position distant from a surface adjacent to the zone under examination and a second position at which the screen comes into contact with the surface. This movable screen allows observation of the skin or the hair by transillumination, i.e., by lighting a zone of the skin or the hair using light coming from adjacent zones. The skin or the hair functions as a light guide, so as to obtain information about transparency. This information can be combined where appropriate with other information drawn from previous observations made under different lighting conditions. The screen can also be brought into a position so that the zone under examination is illuminated by grazing light. The screen can include a tubular wall which, in use, extends around the zone under examination. The screen, which can be of non-circular section, can include a conical or pyramid-shaped portion that converges towards the zone under examination. The device can include at least one spring configured to urge the screen into a rest position when not in use.

The device can include a reticule so that the distance from which light diffusion is no longer visible can be measured when observing under transillumination. In a preferred embodiment, the device includes at least one color filter. The filter can be blue in color, for example, so as to reveal skin pigmentation.

In another preferred embodiment, the device includes at least one polarizer. The polarizer can be placed on the path of the light between a light source and the zone under examination. The device can also include at least one polarizer placed on the path of the light between the zone under examination and the eye of the observer. The device can include at least two polarizers of different orientations that are juxtaposed, and are placed on the path of the light between the zone under examination and the eye of an observer. This feature enables the user to observe contrast between two zones of the image, and to take advantage of the rather high sensitivity of the human eye to contrast. The device can include at least one polarizer pivotally mounted so as to enable the user to vary the orientation of its direction of polarization relative to a reference direction. Under such circumstances, the device can include, for example, a handle incorporating an actuator member such as a knurled knob, for example, enabling the orientation of the polarizer to be varied using the same hand as is holding the handle.

The device can be configured to illuminate the zone under examination with natural light. The device can include a skirt of transparent plastic material having an edge which can be placed around the zone under examination.

The device can also include at least one integrated light source. The integrated light source can include at least one light emitting element selected from the following: an incandescent lamp; a light emitting diode (LED); a fluorescent lamp. The device can include light emitting elements that illuminate in respective different wavelength ranges. By way of example, the device can include a source that reproduces the spectral characteristics of natural light, possibly including slightly-colored light emitting diodes. The device can include a plurality of the light emitting sources together with a control mechanism configured to control at least a fraction of light emitting sources to be powered selectively. The device can include light emitting elements disposed in a circle.

The device can also include a housing configured to receive one or more electrical batteries. Such a housing can present an axis that is substantially perpendicular to an observation direction for observing the zone under examination.

The device can include a pane enabling the skin in the zone under examination to be compressed so as to expel blood therefrom. Such a pane can be made of glass or of transparent plastic material. The pane can optionally be colored. Such a pane can be a removable accessory or it can be an element that is permanently fixed to the device. The pane can be movable between an active position, in which it is interposed between the skin and the light path leading to the observer, and an inactive position, in which the pane is not situated on the light path leading to the observer. The device can include a ring configured to secure a camera thereto.

In a particular embodiment, the device includes or is coupled to an atlas of reference images. These images can be placed on a single medium or they can be connected together. Each image can be associated with a respective alphanumeric indication. The device can also be coupled to a computer configured to display the reference images.

The observation device can also include or be used in combination with a tool configured to crease or stretch the skin. By way of example, such a tool can include two portions configured to press against the skin and capable of being moved apart or moved towards each other in order to stretch or crease the skin. On each of its portions for pressing against the skin, the tool can include a strip of double-sided adhesive configured to adhere to the skin. The tool can be fixed on the observation device. At least one difference between the images observed through the observation device can be the extent to which the skin is creased or stretched.

The tool for creasing or stretching the skin can also be used independently of the observation device. The invention thus also provides, independently of the above-specified observation device, a tool for evaluating the skin. The tool can include two portions for pressing against the skin and interconnected by a connection that moves them relative to each other between a position at which the tool is placed on the skin, at which the two portions are close together, and a position at which the skin is stretched, at which the two portions are moved apart. The connection can include at least one resilient member urging the two portions apart.

The two portions can thus be moved towards each other against the action of the resilient member, then placed on the skin, and then released. The resilient member can then urge them apart or can assist the user in moving them apart manually. The connection between the two portions can be configured to space the two portions apart to a predetermined distance. The connection can include, for example, at least one abutment determining the maximum spacing of the two portions. The connection can be configured to provide a hard point during displacement of the two portions when they reach their maximum spacing. For example, the connection can include at least one locking member which engages on reaching maximum spacing. By way of example, each of the two portions can be generally U-shaped when the tool is observed from above, in a direction perpendicular to the direction in which the two portions move relative to each other. The two portions can be interconnected by two rods, with one of the rods being fixed to one of the portions and the other rod being fixed to the other portion. Preferably, each rod that is fixed to one of the portions can slide in a housing of the other portion. The housing can pass through one of the limbs of the U-shape. The two portions can be configured such that when they are in their close-together position, they form a window for observing the skin. When the two portions are each U-shaped, this window is formed by the concave areas of the U-shapes.

A material suitable for taking an imprint, for example, a wax or a resin, can be cast into the above-mentioned window both when the two portions of the tool are in the close-together position and when they are in the spaced-apart position, for example, in order to compare the appearance of the skin in the stretched state or the non-stretched state at successive time intervals. The tool for stretching the skin can be used in particular for revealing microcysts or other defects of the skin. The stretching tool can also be configured so as to measure the spacing between the two portions when pressed against the skin solely under drive from the resilient member. A greater or smaller amount of spacing between the two portions can be representative of greater or lesser capacity of the skin for being stretched. When the connection between the portions includes rods as defined above, one of the above-specified rods can include graduations enabling the user to measure the spacing between the two portions.

The invention also provides a method in which the above-defined stretching tool is used. This method can include the step of placing on the skin a tool including two applicator portions interconnected by a connection that enables the spacing between them to be modified, the two portions being movable in translation relative to each other. For example, each of the two portions are preferably secured to the skin by a double-sided adhesive tape. The portions can be placed on the skin while they are positioned close-together. The method can also include the step of moving the two portions so as to stretch the zone of the skin that is situated between them. The two portions can be spaced apart, for example, solely under the drive from at least one resilient member and/or under spacing drive from a user. The two portions can be maintained with a predetermined spacing while the skin is being observed.

The invention also provides a method of evaluating the degree of a characteristic of body typology, the method including the step of observing the skin or the hair by with the observation device as discussed above. The observed images can be compared with reference images in order to select a reference image. In a particular embodiment of the method, contrast is observed between light including both a reflection component and a backscattered component and light including essentially a backscattered component. The contrast can be achieved, for example, by illuminating the zone under examination with polarized light and by observing it through a polarization analyzer. The reference images can be displayed on a computer screen, as mentioned above. The reference images can be transmitted to the computer from a server over a computer network, prior to being displayed on the screen.

The method can further include the step of transmitting to the server an indication that is representative of the selected reference image. The server can then be programmed as to establish a diagnosis, for example, or else to recommend a cosmetic or a care product.

In a particular implementation of the invention, a characteristic of body typology is evaluated, treatment is performed, and then a new evaluation is performed in order to detect any variation in the characteristic and to determine the effectiveness of the treatment. Preferably, the treatment performed has an effect on the characteristic evaluated.

As mentioned above, the same observation device can be used to perform successively or simultaneously at least two types of observation selected from the following:

I. observation under diffuse lighting;
II. observation under grazing light;
III. observation under directional lighting;
IV. observation by transillumination;
V. observation under polarized light using a non-crossed polarizer;
VI. observation under polarized light using a crossed polarizer;
VII. observation while compressing the skin;
VIII. observation without compressing the skin;
IX. observation while stretching the skin;
X. observation without stretching the skin;
XI. observation while creasing the skin; and
XII. observation without creasing the skin.

The types of observation selected can be, for example, I and II, V and VI, VII and VIII, IX and X, or XI and XII. When performing observations IX and X, or XI and XII, the method can include a step of, prior to observing the zone of the skin using the above-described device, applying a skin stretching or creasing tool (e.g., a tool as defined above) to the zone of the skin, and in stretching or creasing the zone of the skin.

According to another embodiment, the invention also provides a method of evaluating the degree of a characteristic of body typology, the method including the step of applying a skin stretching or creasing tool to the skin; optionally taking an imprint of the zone of the skin prior to stretching or creasing; stretching or ceasing the zone of the skin; taking a new imprint of the zone of the skin; and observing the imprint(s) as obtained in this way with the above-defined observation device.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 15 shows another example of the device according to another embodiment of the present invention in an exploded perspective view;

FIG. 16 is an end view seen looking along arrow XVI of FIG. 15;

FIG. 17 shows a variant of a portion of the device of FIG. 15;

DETAILED DESCRIPTION OF THE PREFERRED EMBODIMENTS

Figure 1:
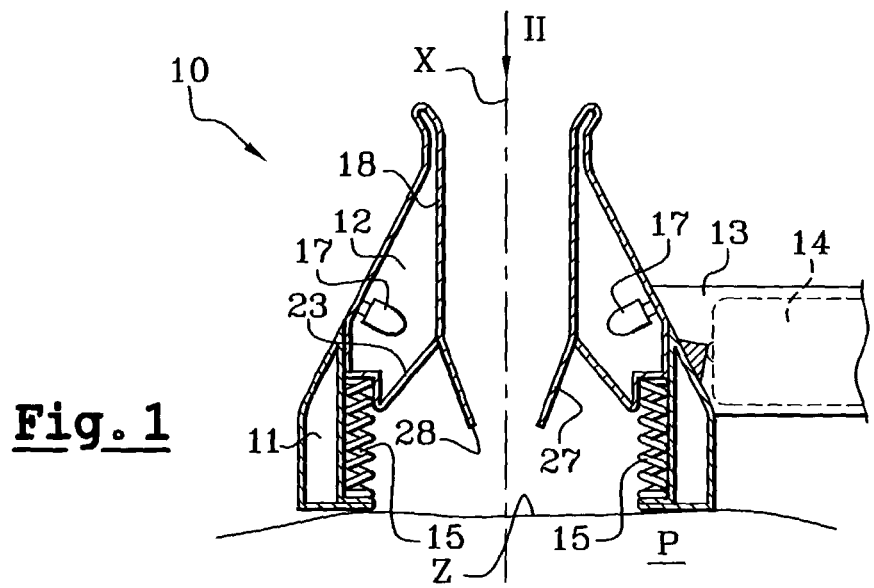
FIG. 1 is a diagrammatic fragmentary axial section view of an optical instrument for implementing according to an embodiment of the present invention.

Referring now to the drawings, wherein like reference numerals designate identical or corresponding parts throughout the several views, a first embodiment of the present invention is in the form of an optical instrument 10 shown in FIGS. 1 to 4 for observing the skin P or the hair. The instrument 10 includes a support 11 for placing the instrument on the surface to be observed, a moving assembly 12 capable of being moved relative to the support 11 along an axis X, and a handle 13 enabling the instrument to be held by a user, the handle 13 being fixed relative to the support 11 and including one or more optionally rechargeable batteries 14.

A resilient return system acts between the support 11 and the moving assembly 12 so as to urge the assembly towards a rest position corresponding to FIG. 1 in which the assembly 12 comes to press against the handle 13. In the example shown, this return system includes a plurality of springs 15 working in compression, each having one end bearing against a shoulder of the support 11 and an opposite end bearing against the assembly 12.

Figure 2:
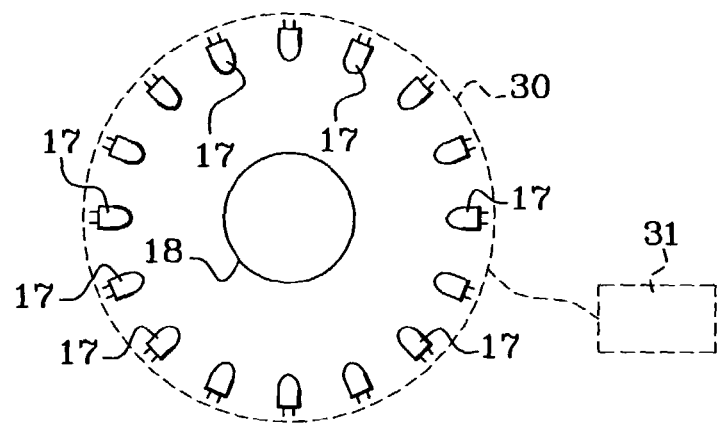
FIG. 2 is a fragmentary plan view as seen looking along arrow II of FIG. 1.

The assembly 12 includes a plurality of light emitters 17, for example, white light emitting diodes distributed around the axis X, as shown in FIG. 2. The light emitters can produce either diffuse lighting of the zone Z under examination when all of the light emitters are powered, or lighting in one or more particular directions, when only a fraction of the light emitters are powered. The light emitters 17 are powered electrically, for example, by the batteries 14 via a power supply circuit 30 which is represented in diagrammatic manner for clarity. The power supply circuit 30 can be connected to a control circuit 31. Observation is performed via a tube 18 of the moving assembly 12.

An optical element 23 is placed on the path of light between the light emitters 17 and the zone Z under examination. In the example shown, this optical element 23 includes a translucent annular piece which can be colorless or colored. This optical element can function as a diffuser. The tube 18 is extended downwards by a screen 27 having a free edge 28, which defines the field of observation. The optical instrument 10 enables the same surface to be observed under different lighting conditions in succession.

Figures 3, 4:
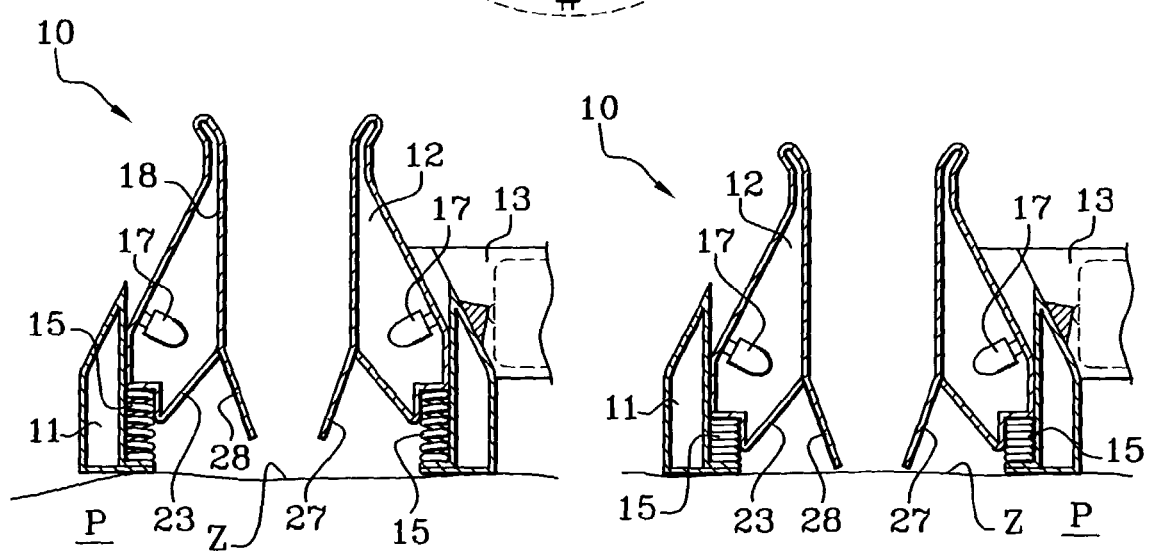
FIG. 3 shows the device of FIG. 1 in a configuration for observation under grazing light.
FIG. 4 shows the device of FIG. 1 in a configuration enabling transillumination.

In the configuration shown in FIG. 1, the zone Z under examination can be illuminated in diffuse and omnidirectional manner by all of the light emitters 17. The screen 27 can be moved towards the zone Z under examination because the assembly 12 is movable relative to the support 11, as shown in FIG. 3. As seen from FIG. 3, the bottom edge 28 of the screen 27 has moved by exerting sufficient downward pressure on the assembly 12 to overcome the action of the return springs 15. This feature enables the zone Z under examination to be illuminated with grazing light, which more clearly reveals the relief of the skin or the hair and increases brilliance.

The user also has the option of pressing fully against the assembly 12 so as to bring the screen 27 into contact with the surface of the skin or the hair, as shown in FIG. 4. Under this configuration, the zone under examination is illuminated solely by transillumination, i.e., by light diffusing through the tissue under observation. This configuration provides information concerning the transparency of the tissue, its color, and the extent to which it is irrigated by blood.

The electrical power delivered to the light emitters 17 can remain unchanged between the various observations. The control circuit 31 can include merely an electrical switch providing on/off control of power delivery to all of the light emitters 17, or it can be more complex. For example, the circuit 31 can power only some of the light emitters 17 in selective manner in order to obtain directional or pluridirectional lighting that can be stationary or rotating. If the light emitters are LEDs of different colors or capable of emitting various different wavelengths, the circuit 31 can modify the spectral characteristics of the light illuminating the zone under examination. Between the various observation configurations for the zone under examination as shown in FIGS. 1, 3, and 4, at least one observation characteristic or feature is modified other than the magnification or the intensity of the integrated light source.

Figure 5:
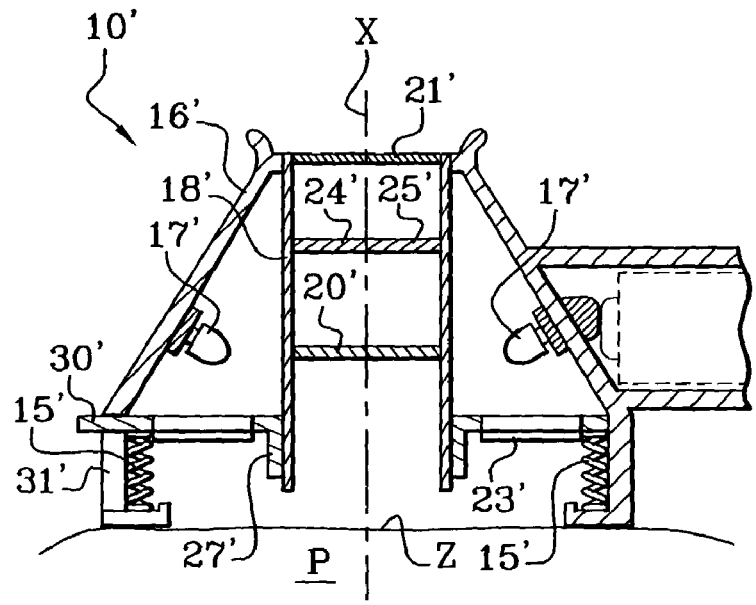
FIG. 5 is a diagrammatic and fragmentary axial section of a device according to another embodiment of the present invention.
Figure 6:
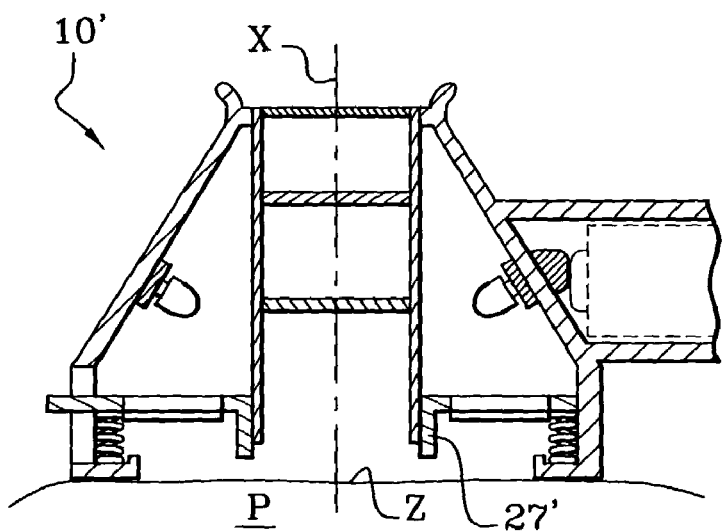
FIG. 6 shows the device of FIG. 5 in a configuration providing grazing lighting.
Figure 7:
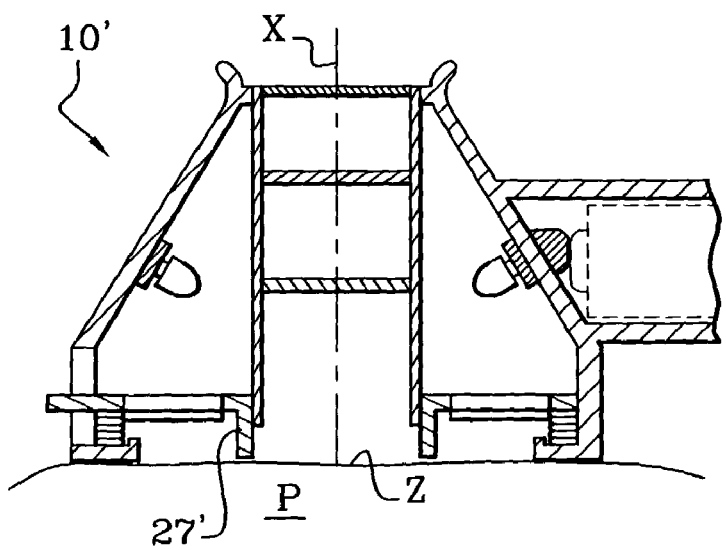
FIG. 7 shows the device of FIG. 5 in a configuration enabling transillumination.

FIGS. 5 to 7 show an optical instrument 10' according to another embodiment of the present invention. In this embodiment, the instrument 10' includes a body 16' which is stationary and a screen 27' which is movable relative to the body 16' along the axis X in order to modify the lighting conditions applied to the zone Z under observation. For example, the lighting conditions can be switched between multidirectional diffuse lighting and grazing light, as shown in FIG. 6 and lighting by transillumination, as shown in FIG. 7.

Figure 8:
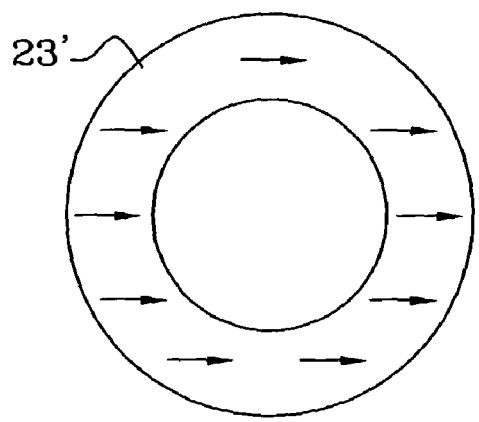
FIG. 8 shows the polarizer of the device of FIGS. 5 to 7 in plan view.

A polarizer 23' shown on its own in FIG. 8 is placed on the path of the light from the light emitters 17' and the zone Z under observation. This polarizer 23' can be annular in shape and can provide polarization in a single direction, as represented by arrows in FIG. 8. Of course the polarizer 23' can have other shapes and other polarization.

The screen 27' is mounted to slide on a tube 18'. The tube 18' supports lenses 20' and 21', and polarizers 24' and 25'. The screen 27' can be moved using a tab 30' which projects out from the instrument through a slot 31' in the body 16' on which the light emitters 17' are mounted. The light emitters 17' can be arranged in the same manner as the light emitters 17 in the assembly of FIGS. 1-4. An advantage of the instrument 10' is that, while changing the lighting configuration by moving the screen 27', the distance between the zone under examination and the lenses 20', 21' does not change.

Figure 9:
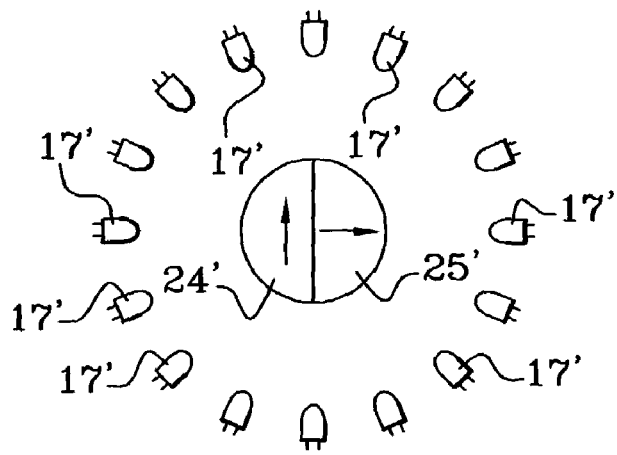
FIG. 9 is a fragmentary plan view showing the analysis polarizer disk of the device of FIGS. 5 to 7.

In the example under consideration, each of the two polarizers 24' and 25' is in the form of a half-disk. The two half-disks are connected together via their bases so as to form a single disk for polarization analysis, of course other polarizer shapes can be used. This disk is placed on the light path in the tube 18' in the image focal plane of the lens 20'. The polarization directions of the polarizers 24' and 25' are perpendicular to each other and are represented by the arrows in FIG. 9.

The polarization analyzer including the polarizers 24' and 25' provides one half-image with brilliance and another half-image without brilliance by selecting the direction of polarization of one of the half-disks 24' and 25' to be parallel to the polarization direction of the polarizer 23'. Where appropriate, the polarizers 24' and 25' are replaced by a single polarizer mounted to turn about the axis X so as to be capable firstly of making its polarization direction coincide with the polarization direction of the incident light and secondly of making its direction of polarization extend subsequently perpendicularly to the polarization direction of the polarizer 23'. The two-part polarization analyzer 24', 25' provides an image that is contrasted, so as to take advantage of the high sensitivity of the human eye to contrast.

Figure 10:
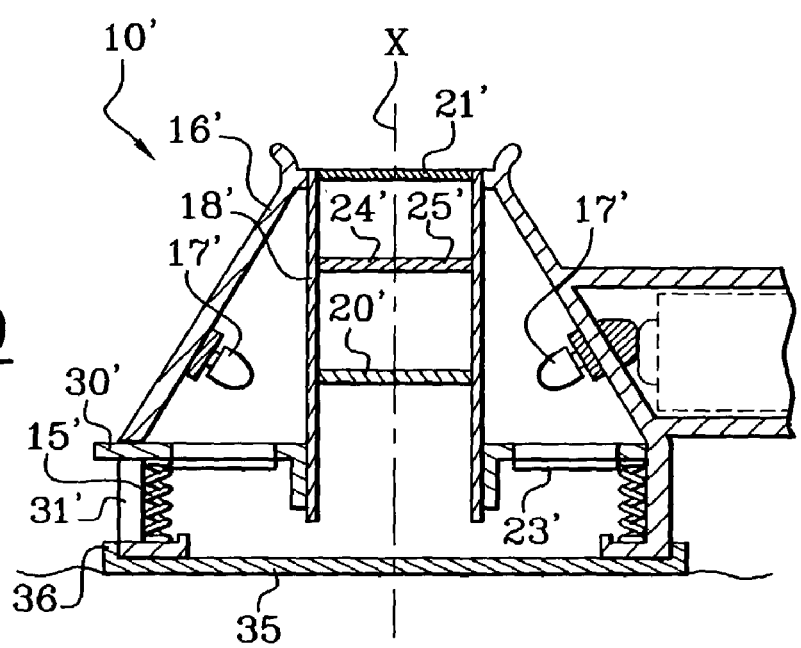
FIG. 10 shows a device according to another embodiment of the present invention.

As shown in FIG. 10, each instrument 10 or 10' can include a pane 35 through which observation is performed. This pane 35 can be made of a plastic material. The pane 35 can have, for example, a rim 36 enabling the pane 35 to be put into position on the instrument 10 and 10'. The pane 35 can be a removable accessory or a retractable accessory remaining secured to the instrument in its retracted position. When in place on the instrument, the pane 35 compresses the skin and expels blood from it. This pane allows observations on the skin while reducing the incidence of blood color on skin color. It is possible to perform one series of observations without the pane 35 and another series of operations with the pane 35 under various types of lighting or polarization, and then to compare the results to extract useful information therefrom.

Figure 11:
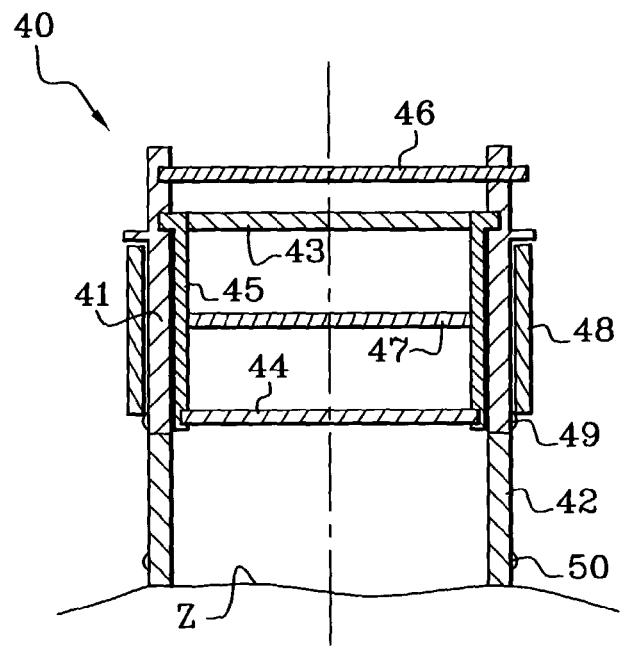
FIG. 11 is a diagrammatic and fragmentary axial section view of another example of an optical instrument according to another embodiment of the present invention.
Figure 12:
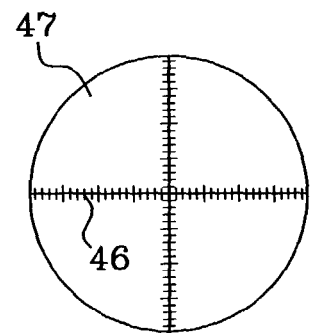
FIG. 12 is a fragmentary plan view of FIG. 11.
Figure 13:
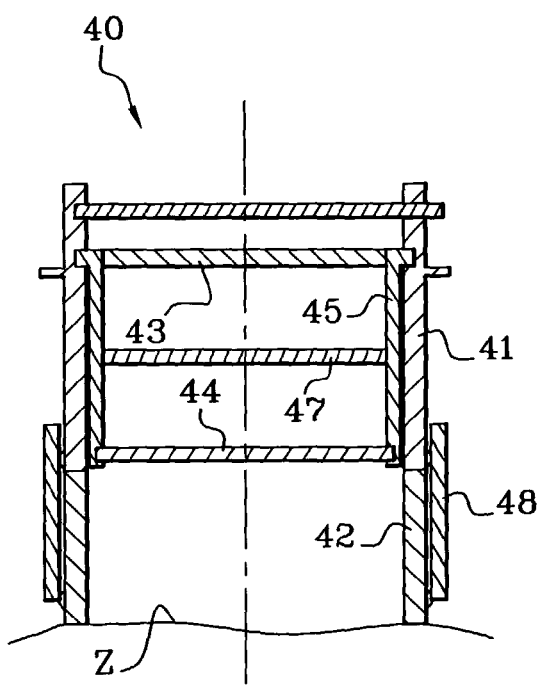
FIG. 13 shows the device of FIG. 11 in a grazing light configuration.

Compared with the instruments 10 and 10' described above, FIGS. 11, 13, and 14 show an instrument 40 without integrated lighting. Thus, while these embodiments provide arrangements for exposing the zone under examination with light, the structure of the instrument need not itself include a light source, as the light source can be provided separately. The instrument 40 includes a body 41 which is extended downwards by a transparent skirt 42. The body 41 serves as a support for an optical assembly including lenses 43 and 44 carried by a tube 45 and snap-fastened in the body 41. The optical assembly also includes a reticule 46 enabling a distance to be measured on the zone under examination. By way of example, FIG. 12 shows a reticule printed on a glass plate 47 placed on the path of light coming from the zone under examination. A color filter 46 is removably mounted in the body 41. In the example shown, the filter is blue so as to emphasize, if so desired, spots of pigmentation.

Figure 14:
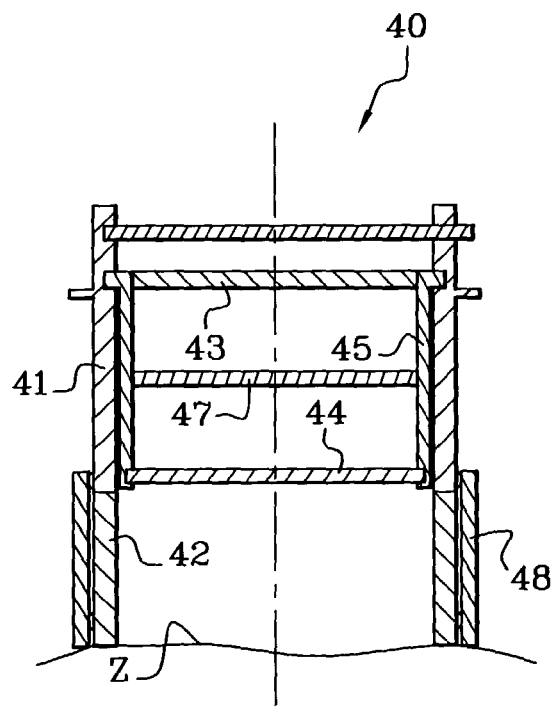
FIG. 14 shows the device of FIG. 11 in a configuration that enables transillumination.

A screen including an opaque ring 48 is slidably mounted on the body 41 and the transparent skirt 42. The ring 48 moves between a fully retracted position corresponding to FIG. 11 in which the ring 48 does not cover the transparent skirt 42, an intermediate position corresponding to FIG. 13, in which the ring 48 covers a major fraction of the transparent skirt 42 so as to allow grazing light only on the zone under examination, and a position in which the ring 48 is fully lowered as shown in FIG. 14 where the ring covers the entire transparent skirt 42 and enables illumination to be performed by transillumination.

In the example shown, projections 49 and 50 are formed on the body 41 and the transparent skirt 42 so as to enable the skirt 48 to be held stationary in each of the above-described configurations. Other positioning mechanisms can be used so as to position the screen 48 at various positions along the skirt 42. These positions are not intended to be limited to three or some other number, but can be any position between the fully retracted position and the fully covered position. When the zone under examination is observed by transillumination, the observer can use the reticule 46 to measure the distance beyond which light diffusion is no longer visible, and thereby gain information concerning the transparency of the skin.

FIG. 15 shows another embodiment of an observation device 120 made in accordance with the invention. The device 120 includes a light source 122, an endpiece 123, and an optical assembly 121. The light source 122 includes a handle 124 forming a housing containing one or more optionally rechargeable batteries, and an open portion 127 in which the optical assembly 121 can be engaged.

The optical assembly includes an eyepiece 128 having one or more lenses (not shown) so as to produce a magnified image, together with a polarizer. The light source 122 includes a selector 126 configured to control the light emitted by the light source 122. For example, the selector 126 can be configured to control the light intensity so that the zone for observation can be illuminated with two or more different light intensities. The selector 126 can also be configured to control the type of light so that the zone for observation can be illuminated with two or more different types of lighting, e.g., one type simulating daylight and another type simulating incandescent lighting.

By way of example, the endpiece 123 is preferably frusto-conical in shape having a base 129 of diameter greater than the field of observation of the optical assembly 121. In the example shown, the diameter of the base 129 is about 40 millimeters (mm) and that of the field of observation is about 30 mm, of course other dimensions are within the scope of the present invention. The dimensions can be designed to reduce or avoid contact pressure between the endpiece 123 and the skin having an influence on the appearance of the zone situated in the field of observation. It is possible to provide magnetic fixing between the endpiece 123 and the light source 122. In addition, by way of example, the endpiece 123 can include a magnetized metal ring. At its end which comes into contact with the skin, the endpiece 123 can include a removable ring.

As can be seen in FIG. 16, the light source 122 includes a plurality of light sources 130. For example, the light sources can be light emitting diodes 130. Each of the diodes 130 can be positioned on an axis substantially parallel to that of the optical assembly 121. The light emitting diodes 130 can be covered by a polarizer 131. The height of the endpiece 123 can be selected so that the illumination on the zone of the skin situated in the field of observation is substantially uniform. As shown in FIG. 17, the device 120 can include a knurled knob 133 enabling the user to turn the optical assembly 121 with the same hand as is used for holding the handle 124.

The observation device 120 can be used as discussed next. The endpiece 123 and the optical assembly 121 can be put into place on the light source 122, after which the user can turn the optical assembly 121 relative to the light source so that the polarizer contained in the optical assembly 121 has the same polarization direction as the polarizer 131 or has a direction that is substantially perpendicular thereto. This makes it possible to observe the skin successively with brilliance and without brilliance. In another embodiment, the optical assembly 121 has two juxtaposed polarizers with directions of polarization that are perpendicular, similar to the example described above with reference to FIG. 9.

Figures 18, 19:
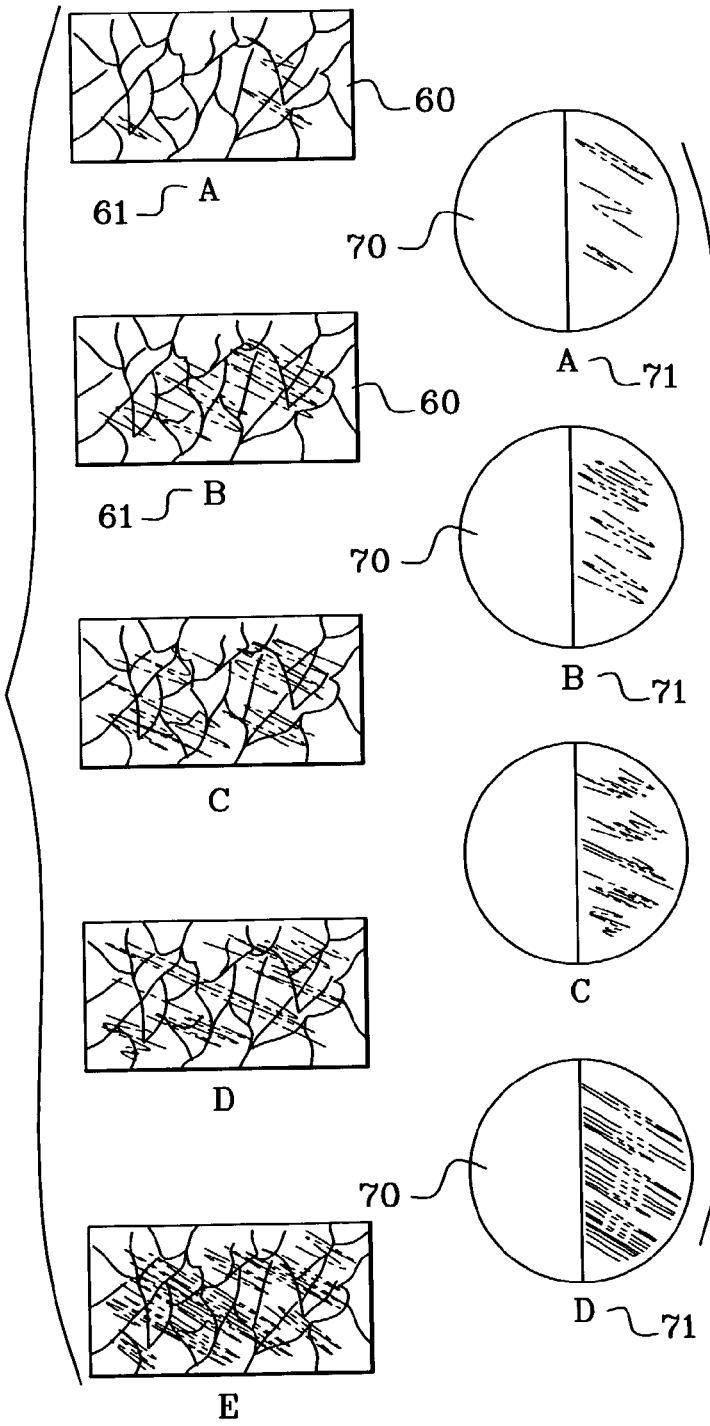
FIG. 18 is a diagrammatic representation of a brilliance atlas according to another embodiment of the present invention.
FIG. 19 is a diagrammatic representation of a contrast atlas according to another embodiment of the present invention.

Each image observed using the optical instruments described above can be compared with a reference image of an atlas including a plurality of reference images. For example, the atlas can include images expressing varying degrees of different characteristics of body typology, in particular the brilliance or the color of the skin, or images corresponding to various degrees of contrast. FIG. 18 is a diagrammatic representation of a brilliance atlas including a plurality of reference images 60 each corresponding to a different degree of skin brilliance, and quantified by an alphanumeric identifier 61.

FIG. 19 is a diagrammatic representation of a contrast atlas (i.e., showing differences in luminosity or color), including a plurality of reference images 70, corresponding to various degrees of contrast or difference that are likely to be observed when using a polarization analyzer of the kind formed by the half-disks 24', 25' as described above. These images 70 are associated with alphanumeric identifiers 71 enabling them to be identified.

Figure 20:
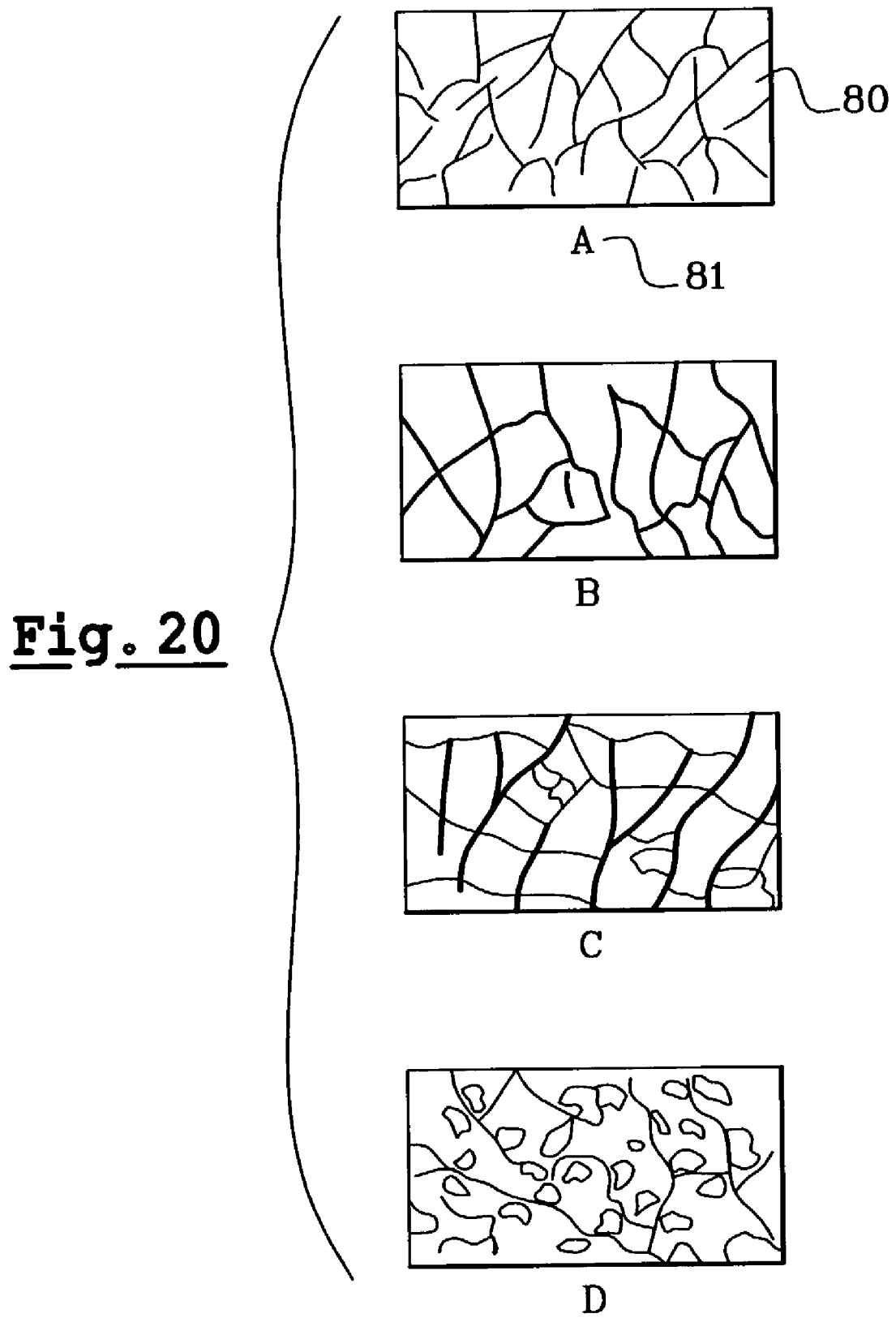
FIG. 20 is a diagrammatic representation of a skin dryness atlas according to another embodiment of the present invention.

FIG. 20 is a diagrammatic representation of an atlas of skin dryness, including a plurality of images 80 each associated with an alphanumeric identifier 81. The images 80 express various degrees of skin dryness, going from severe desquamation, characteristic of extremely dry skin, to no desquamation, representing normal skin.

Figure 21:
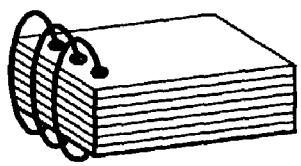
FIG. 21 shows an atlas of bound images according to another embodiment of the present invention.
Figure 22:
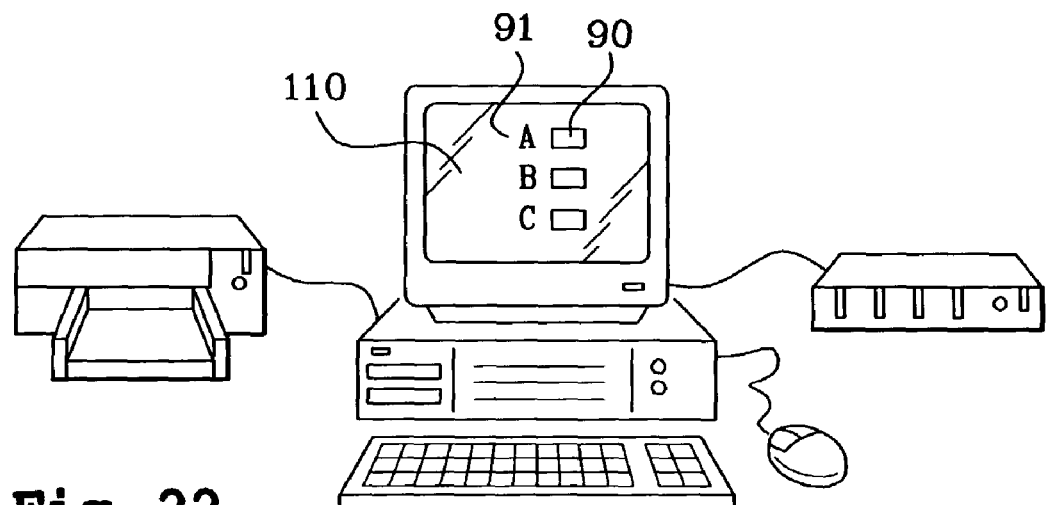
FIG. 22 is a diagram showing a computer enabling reference images to be displayed on a screen according to another embodiment of the present invention.
Figure 23:
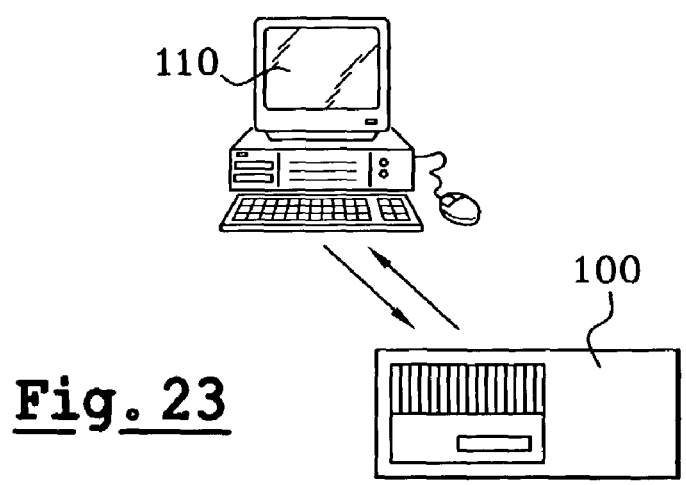
FIG. 23 is a diagram showing a computer suitable for displaying reference images connected to a remote server according to another embodiment of the present invention.

The reference images in an atlas can be printed on a common medium, or a plurality of media can be bound together, as shown in FIG. 21. Reference images can also be displayed on the screen of a computer 110, as shown in FIG. 22, each image being associated with an alphanumeric identifier. The results of an evaluation can be transmitted remotely to a server 100 over a computer network, in particular the Internet, from the computer 110, as shown in FIG. 23. The server 100 can be configured to provide a diagnosis as a function of the results transmitted to it, and where appropriate to recommend a cosmetic or care product.

When the reference images are displayed on the screen of a computer, these images can be transmitted by the server 100 after the user has connected to the corresponding Internet site. The invention can be implemented in such a manner as to track the effectiveness of a course of treatment, with evaluation being performed after each stage of treatment, and with the results of successive evaluations being compared.

Because of the possibility of using a single optical instrument to obtain information concerning brilliance, color, relief, and transparency, and by using an atlas that enables such information to be quantified, the present invention makes it is possible to create a multi-vector databank bringing together vectors each corresponding to a particular individual, each vector having at least two components each constituted by the result of an observation performed using the same optical instrument.

Figure 24:
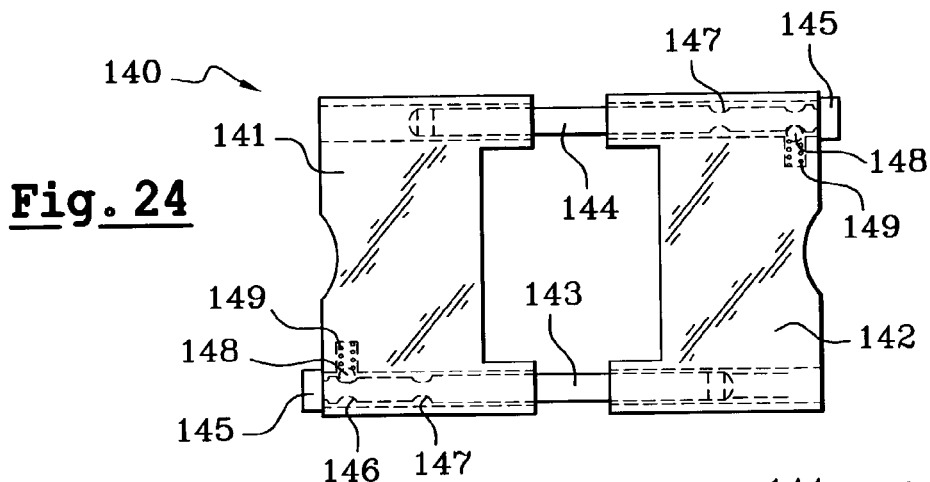
FIGS. 24 and 25 are a diagrammatic plan view of a tool for creasing the skin with the portions for pressing against the skin being shown respectively in the spaced-apart and in the close-together positions.
Figure 25:
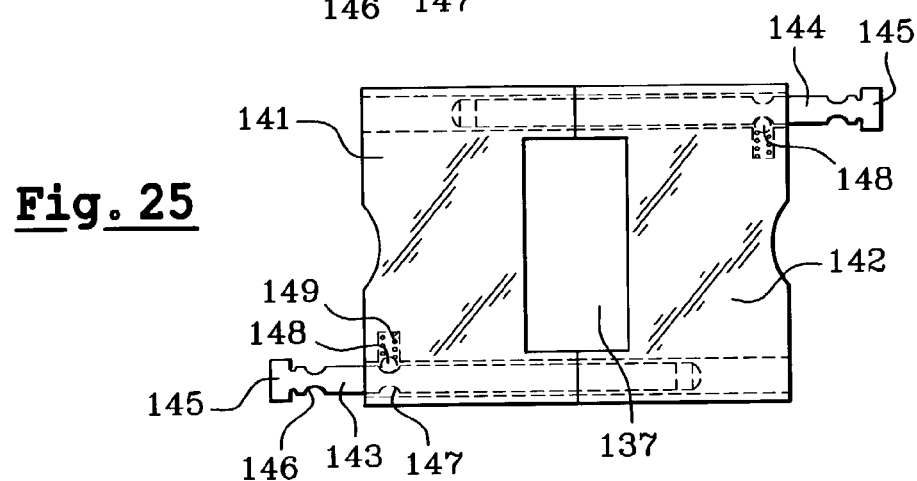

The observation devices described above can be used in combination with a tool, enabling the skin to be creased or stretched. FIGS. 24 and 25 show an example of a tool 140 enabling the skin to be creased or stretched. The tool 140 shown in these figures includes two portions 141 and 142 for pressing against the skin and connected to each other by a connection that enables them to be moved relative to each other.

In the example shown, each of these portions 141 and 142 are U-shaped. When the two portions are moved close together, as shown in FIG. 25, they define between them a window 137 for observing the skin. This window is formed by the concave areas of the U-shapes in the embodiment shown in FIG. 25. The portions 141 and 142 can be connected together in various ways. The present invention is not limited to U-shaped portions, but can include portions with different shapes that define observation windows.

In the example described, the connection includes two rods 143 and 144 having axes that are parallel. The rod 143 is fixed at one end in the portion 142 and is slidably received in a housing in the portion 141. The opposite end of the rod 143 has an enlarged head connected to the remainder of the rod so as to form a groove 146. The rod 143 also has a second groove 147, and the portion 141 has a ball 148 biased by a spring 149 to press against the rod 143. The same applies to the rod 144 which is stationary relative to the portion 141 and which slides in a housing of the portion 142.

In the spaced-apart position of the portions 141 and 142, each ball 148 engages in the corresponding groove 146 enabling the two portions 141 and 142 to be held stationary in their spaced-apart position. When the portions 141 and 142 are moved towards each other, each of the balls 148 engages in the corresponding groove 147. These features makes it possible to create a hard point feeling whenever the two portions are in the spaced-apart position or the close-together position. Other mechanisms configured to position the portions 141 and 142 in the open and closed configuration are within the scope of the present invention.

The tool 140 can be put into place on the skin by placing double-sided adhesive tape on each of the portions 141 and 142. It is then possible using one of the observation devices described above to proceed with two observations, one when the skin is not creased (e.g., after the tool 140 has been placed on the skin with its portions in the spaced-apart position as shown in FIG. 24), and the other after the skin has been creased (e.g., after the portions 141 and 142 have been moved towards each other as shown in FIG. 25). The observation device can be configured as to co-operate with the tool 140.

It is also possible to perform an observation when the skin is in a non-stretched state (e.g., after the tool 140 has been placed on the skin with the portions 141 and 142 being in the close-together state, as shown in FIG. 25), followed by an observation with the skin in the stretched condition (e.g., after the portions 141 and 142 have been moved into the spaced-apart position, as shown in FIG. 24).

Figure 26:
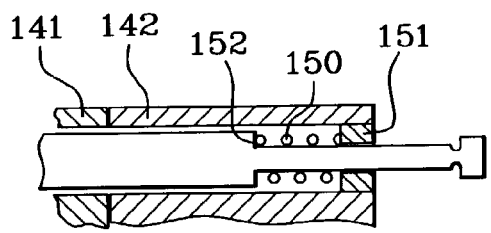
FIGS. 26 and 27 are section views through a tool for stretching the skin, when the tool is in its configuration for being put into place on the skin and for stretching the skin.
Figure 27:
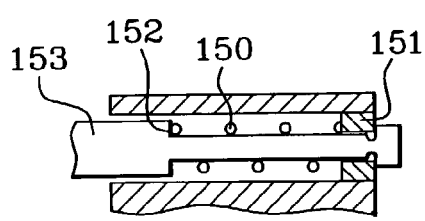

In order to make it easier to move from the close-together position shown in FIG. 25 to the spaced-apart position shown in FIG. 24, the tool 140 can advantageously be provided with at least one resilient member. For example, the resilient member can include a coil spring 150 engaged on one of the rods, as shown in FIGS. 26 and 27. Each of the rods 143 or 144 can be provided with a corresponding spring 150. As shown in FIG. 26, the spring 150 can bear at one end against a ring 151 fixed on one of the portions that is to be applied to the skin, and at its other end it can come to bear against a shoulder 152 of the rod. The spring 150 is in the compressed state when the two portions 141 and 142 are close together. The tool can thus be placed on the skin while the portions 141 and 142 are close together, with each spring 150 being in the compressed condition, after which the portions 141 and 142 can be moved apart under drive from the springs 150 relaxing. At least one of the rods 143 or 144 can have graduations 153 which are visible to the user as the portions 141 and 142 move apart, thus making it possible to determine accurately how far the two portions 141 and 142 have moved apart.

Figure 28:
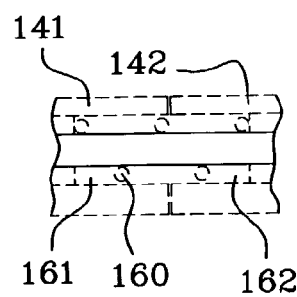
FIG. 28 shows a portion of a tool according to another embodiment of the present invention.

Naturally, within the scope of the present invention, it is possible to use at least one resilient member disposed in some other manner. For example, a coil spring 160 working in compression can be engaged on one of the rods 143 and 144, having its ends bearing against the end walls of housings 161 and 162 and facing each other on the portions 141 and 142, the housings being formed in the limbs of the U-shapes, as shown in FIG. 28. Where appropriate, the device shown in FIG. 28 can be incorporated in addition to the grooves 146 and 147 and the balls 148 of the example shown in FIGS. 24 and 25.

Naturally, the invention is not limited to the examples described above and the structure of the optical instrument can be modified, in particular by replacing the light emitting diodes with other lighting sources, such as incandescent lamps or fluorescent lamps, for example. When a screen is used for observation by transillumination, the screen can be constituted by a separate element that is releasably applied to the optical instrument.

Obviously, numerous modifications and variations of the present invention are possible in light of the above teachings. It is therefore to be understood that within the scope of the appended claims, the invention may be practiced otherwise than as specifically described therein.

What is claimed as new and desired to be secured by Letters Patent of the United States is:

1. A hand held portable device for observing at least one characteristic of appearance of the skin or the hair, comprising:
    an integrated light source configured to generate light,
    means for exposing a zone of the skin or the hair under examination with said light from said light source,
    means for generating at least two images of said zone under examination, said images differing from each other as to a feature other than magnification and the intensity of said light, and
    an aperture that allows a user to observe said zone of the skin or the hair under direct examination by looking through said aperture of the hand held portable device during operation of the hand held portable device, the device being configured to observe said zone under examination according to different configurations, one of said different configurations being exposing said zone to lighting by transillumination.

2. A device according to claim 1, wherein said means for generating generates said images in succession and includes a member which varies said feature other than said magnification and said intensity of said light.

3. A device according to claim 1, wherein said means for generating comprises optical elements which generate two different images of said zone under examination simultaneously.

4. A device according to claim 1, wherein said means for generating comprises at least one polarizer which varies the orientation of a polarization direction for said images.

5. A device according to claim 1, wherein said means for exposing varies a degree of directivity of said light.

6. A device according to claim 1, wherein said means for exposing varies a direction of incidence of said light.

7. A device according to claim 6, wherein said means for generating comprises a filter which filters the light coming from said zone under examination.

8. A device according to claim 1, wherein said means for exposing varies a color of said light.

9. A device according to claim 1, wherein said means for generating varies a pressure applied to said zone under examination.

10. A device according to claim 1, wherein said means for generating comprises an optical system which magnifies an image of said zone under examination.

11. A device according to claim 1, wherein said means for exposing exposes said zone under examination to diffuse lighting.

12. A device according to claim 1, wherein said means for exposing exposes said zone under examination to directional lighting.

13. A device according to claim 1, wherein said means for exposing exposes said zone under examination to grazing light.

14. A device according to claim 1, wherein said means for exposing comprises at least one screen movable to a position between said light source emitting said light and said zone under examination.

15. A device according to claim 14, wherein said screen is positioned so as to expose said zone under examination to lighting by transillumination.

16. A device according to claim 14, wherein the screen is movable from a first position at which the screen is remote from a surface surrounding said zone under examination and a second position at which the screen comes into contact with said surface.

17. A device according to claim 14, wherein the screen is movable so that said zone under examination is exposed to grazing light.

18. A device according to claim 14, wherein the screen comprises a tubular wall extendable around said zone under examination.

19. A device according to claim 18, wherein the screen comprises a portion which is conical or pyramid-shaped, converging towards said zone under examination.

20. A device according to claim 14, wherein:
    the screen is movable, and
    the device further comprises at least one spring which urges the screen towards a rest position.

21. A device according to claim 1, wherein said means for generating comprises at least one color filter.

22. A device according to claim 21, wherein the filter is blue in color.

23. A device according to claim 1, further comprising at least one polarizer.

24. A device according to claim 1, wherein said means for exposing comprises at least one polarizer placed on the path of light between said light source and said zone under examination.

25. A device according to claim 1, wherein said means for generating comprises at least one polarizer placed on the path of the light between the zone under examination and an observer's eye.

26. A device according to claim 1, wherein said means for generating comprises at least two polarizers of different orientations that are juxtaposed and placed on the path of light between the zone under examination and an observer's eye.

27. A device according to claim 1, further comprising at least one pivotally-mounted polarizer so as to enable a user to modify the orientation of its direction of polarization relative to a reference direction.

28. A device according to claim 1, wherein said means for exposing are configured to expose the zone under examination to natural light.

29. A device according to claim 28, wherein said means for exposing comprises a skirt of transparent plastic material, the skirt having an edge extending around said zone under examination.

30. A device according to claim 1, wherein the integrated light source comprises at least one light emitting element selected from the group consisting of an incandescent lamp, a light emitting diode, and a fluorescent lamp.

31. A device according to claim 30, wherein the integrated light source comprises light emitting elements emitting light in respective different wavelength ranges.

32. A device according to claim 1, wherein the integrated light source comprises a plurality of light emitting elements and control means for selectively powering at least a fraction of said light emitting elements.

33. A device according to claim 1, wherein said integrated light source comprises light emitting elements disposed in a circle.

34. A device according to claim 1, further comprising a housing enclosing one or more electric batteries for powering said integrated light source.

35. A device according to claim 34, wherein the housing has an axis substantially perpendicular to an observation direction for observing said zone under examination.

36. A device according to claim 1, further comprising a pane which compresses the skin in said zone under examination so as to expel blood therefrom.

37. A device according to claim 36, wherein said pane is removable.

38. A system for examining a zone of a body, comprising:
a device according to claim 1; and
an atlas of reference images.

39. A system for examining a zone of a body, comprising:
a device according to claim 1; and
a computer which displays reference images.

40. A device according to claim 1, wherein said means for generating comprises a reticule.

41. A device according to claim 1, wherein said zone under examination is a zone of skin, and said device further comprises a tool for creasing or stretching said skin.

42. A method of evaluating a characteristic of a body, the method comprising the step of observing an image of skin or hair with the device of claim 1.

43. A method according to claim 42, further comprising the steps of:
comparing the observed image with reference images; and
selecting a reference image based on said comparing step.

44. A method according to claim 43, wherein the observing step comprises observing a contrast between light which comprises both a reflected component and a backscattered component and light which essentially comprises a backscattered component.

45. A method according to claim 43, further comprising displaying the reference images on a screen of a computer.

46. A method according to claim 45, further comprising transmitting the reference images to the computer from a server over a computer network prior to the displaying step.

47. A method according to claim 46, further comprising transmitting to the server an indication representative of the selected reference image.

48. A method according to claim 42, further comprising the steps of illuminating the zone under examination with polarized light, and observing said zone with a polarization analyzer.

49. A method according to claim 42, wherein a same device is used successively or simultaneously to perform at least two types of observation selected from the group consisting of:
observation under diffuse lighting;
observation under grazing light;
observation under directional lighting;
observation by transillumination;
observation under polarized light using a non-crossed polarizer;
observation under polarized light using a crossed polarizer;
observation while compressing the skin;
observation without compressing the skin;
observation while stretching the skin;
observation without stretching the skin;
observation while creasing the skin; and
observation without creasing the skin.

50. A method according to claim 42, further comprising the steps of:
performing a cosmetic treatment; and
observing another image of said skin or hair in order to detect any change in said characteristic and to determine the effectiveness of the treatment.

51. A method according to claim 42, wherein the step of observing is performed by transillumination and further comprises the step of measuring a distance beyond which light diffusion is no longer visible.

52. A device according to claim 1, further comprising:
an assembly containing said means for exposing,
wherein said integrated light source is integrated inside said assembly.

53. A device according to claim 52, further comprising:
a handling portion configured to be held by a user, said assembly being coupled to said handling portion.

54. A device according to claim 52, wherein the integrated light source comprises at least one light generating element selected from the group consisting of an incandescent lamp, a light emitting diode, and a fluorescent lamp.

55. A device for observing a zone of a body, comprising:
a support;
an assembly defining a viewing element through which said zone can be observed directly by looking through the device without a photographic or video device; and
an optical element positioned on a path of a light incident on said zone, said optical element being movable relative to said support along a longitudinal axis of the support,
wherein said optical element changes an incidence of said light on said zone when said optical element moves from a first position to a second position, and
wherein the device is configured to observe said zone under examination according to different configurations, one of said different configurations being exposing said zone to lighting by transillumination.

56. A device according to claim 55, wherein said optical element comprises a screen.

57. A device according to claim 55, wherein said optical element comprises a polarizer.

58. A device according to claim 55, further comprising a light source coupled to said assembly.

59. A device according to claim 58, wherein said light source comprises a plurality of light emitting diodes.

60. A device according to claim 55, wherein said assembly comprises a polarizer.

61. A device according to claim 60, wherein said assembly comprises two polarizers.

62. A device according to claim 55, wherein said assembly comprises a lens.

* * * * *